United States Patent
Cinbis et al.

(10) Patent No.: US 9,042,983 B2
(45) Date of Patent: May 26, 2015

(54) IMPLANTABLE SYSTEM FOR FLOW MEASUREMENT INCLUDING CHARGE AMPLIFIER

(75) Inventors: Can Cinbis, Shoreview, MN (US);
Bozidar Ferek-Petric, Zagreb (CR);
Branko Breyer, Zagreb (CR)

(73) Assignee: Medtronic, Inc., Minneapolis, MN (US)

( * ) Notice: Subject to any disclaimer, the term of this patent is extended or adjusted under 35 U.S.C. 154(b) by 1897 days.

(21) Appl. No.: 11/930,583

(22) Filed: Oct. 31, 2007

(65) Prior Publication Data
US 2009/0112275 A1 Apr. 30, 2009

(51) Int. Cl.
*A61N 1/00* (2006.01)
*A61N 1/05* (2006.01)
*A61B 5/027* (2006.01)
*A61N 1/365* (2006.01)
*A61N 1/08* (2006.01)
*A61N 1/375* (2006.01)

(52) U.S. Cl.
CPC . *A61N 1/056* (2013.01); *A61N 1/08* (2013.01); *A61N 1/375* (2013.01); *A61B 5/027* (2013.01); *A61N 1/36514* (2013.01); *A61N 1/36571* (2013.01)

(58) Field of Classification Search
CPC ........... A61N 1/00; A61N 1/025; A61N 1/08; A61N 1/04; A61N 1/372; A61M 1/00; A61B 5/00; A61B 5/03
See application file for complete search history.

(56) References Cited

U.S. PATENT DOCUMENTS

| | | | |
|---|---|---|---|
| 4,432,372 A | | 2/1984 | Monroe |
| 5,197,467 A | * | 3/1993 | Steinhaus et al. ............... 607/20 |
| 5,243,976 A | | 9/1993 | Ferek-Petric et al. |
| 5,267,569 A | | 12/1993 | Lienhard |
| 5,316,001 A | | 5/1994 | Ferek-Petric et al. |
| 5,602,342 A | | 2/1997 | Strandberg |
| 5,785,657 A | | 7/1998 | Breyer et al. |
| 5,799,350 A | | 9/1998 | Ferek-Petric et al. |
| 5,999,848 A | * | 12/1999 | Gord et al. ........................ 607/2 |
| 6,015,387 A | | 1/2000 | Schwartz et al. |

(Continued)

FOREIGN PATENT DOCUMENTS

WO    WO 2008/139347    11/2008

OTHER PUBLICATIONS

Ferek-Petric, Bozidar, Introduction, Cardiac Pacing Based on Intracardiac Flow Measurement, Nov. 2, 2005, pp. 1.1-1.6, University of Zagreb Faculty of Electrical Engineering and Computing, Zagreb, Croatia.

(Continued)

*Primary Examiner* — Christopher D Koharski
*Assistant Examiner* — Elizabeth K So
(74) *Attorney, Agent, or Firm* — Evans M. Mburu; Stephen W. Bauer

(57) ABSTRACT

An implantable medical device lead having a flow measurement sensor mounted thereon is provided with a capsule mounted proximate to the sensor. The capsule is used to house electrical circuitry corresponding to the sensor in order to prevent impedance on conductors of the lead, which gradually decreases over chronic periods, from directly affecting signal transmission between the sensor and the electrical circuitry. The electrical circuitry includes a charge amplifier used for processing signals from the sensor. In some cases, the amplifier can be initially calibrated and periodically tuned so as to have consistent functioning with the sensor over chronic periods.

11 Claims, 7 Drawing Sheets

(56) References Cited

U.S. PATENT DOCUMENTS

| | | |
|---|---|---|
| 6,754,532 B1 | 6/2004 | Ferek-Petric |
| 7,775,966 B2 * | 8/2010 | Dlugos et al. .................... 600/37 |
| 2007/0034017 A1 * | 2/2007 | Winston et al. ............ 73/861.42 |

OTHER PUBLICATIONS

Ferek-Petric, Bozidar, Clinical Utility of the System, Cardiac Pacing Based on Intracardiac Flow Measurement, Nov. 2, 2005, pp. 2.1-2.18, University of Zagreb Faculty of Electrical Engineering and Computing, Zagreb, Croatia.

Ferek-Petric, Bozidar, Non-Doppler flow Measurement Methods, Cardiac Pacing Based on Intracardiac Flow Measurement, Nov. 2, 2005, pp. 3.1-3.18, University of Zagreb Faculty of Electrical Engineering and Computing, Zagreb, Croatia.

Ferek-Petric, Bozidar, Doppler Ultrasonic Blood Flow Measurement, Cardiac Pacing Based on Intracardiac Flow Measurement, Nov. 2, 2005, pp. 4.1-4.27, University of Zagreb Faculty of Electrical Engineering and Computing, Zagreb, Croatia.

Ferek-Petric, Bozidar, Theory—Electrochemical Flow Sensor, Cardiac Pacing Based on Intracardiac Flow Measurement, Nov. 2, 2005, pp. 5.1-5.13, University of Zagreb Faculty of Electrical Engineering and Computing, Zagreb, Croatia.

PCT Search report, PCT/US2008/080864, 3 pages, Feb. 9, 2009.

* cited by examiner

IMPLANTABLE SYSTEM FOR FLOW MEASUREMENT INCLUDING CHARGE AMPLIFIER

BACKGROUND

The present invention generally relates to a flow measurement system, with certain embodiments relating to measurement of blood flow characteristics within the heart and large blood vessels using the system for the purpose of controlling electrotherapy.

Physiologic cardiac pacing is very important on a temporary as well as permanent basis. Temporary pacing is usually applied either after cardiac surgery or during myocardial infarction because of the transient conduction disturbance or arrhythmia. Patients at rest have significantly improved cardiac output when ventricular contraction is synchronous with atrial filling of ventricles. This provides for faster recovery after surgery or from myocardial infarction. Furthermore, some arrhythmias like supraventricular tachycardias and extrasystolies may be prevented by means of physiologic pacing. While temporary pacing can be effectively used to aid certain patients as described above, permanent pacing is often necessary for patients having chronic conduction and rhythm disturbance.

As is known, there are two basic modes of physiologic cardiac pacing: sequential and synchronous. For example, sequential atrio-ventricular pacing can be used to restore normal atrio-ventricular relationships. In this mode, an atrium and a ventricle are paced by twin stimuli separated by an appropriate physiologic interval. However, the heart rate is controlled by the pacemaker program and does not vary according to the physiological needs. In contrast, synchronous cardiac pacing approximates most closely to normal cardiac rhythm. The spontaneous atrial electrogram (P-wave) is sensed by an electrode usually in contact with the atrial endocardium. This is used to trigger the ventricle after an appropriate preset delay. Because the atrial rhythm is paced by a patient's natural pacemaker sinus-atrial node, the frequency varies naturally according to the body workload. Therefore, the P-wave synchronous ventricular cardiac pacing can be considered closest to physiologic rate-responsive pacing.

In recent years, cardiac electrotherapy systems have been designed with flow measurement capability. Such functionality allows for measuring a characteristic of blood flow through a specific region of the heart. In some systems, the characteristic may involve blood flow velocity and can be provided through use of a Doppler ultrasonic transducer, which is mounted on a cardiac pacing lead in spaced relation to a pacing electrode at a distal end of the lead. In some cases, when the pacing lead is inserted in the heart, the pacing electrode is placed at an apex of the right ventricle while the Doppler transducer is positioned at or near the tricuspid valve. The flow velocity transducer is generally formed as an annular piezo body having associated electrodes, and is used to measure the flow velocity by means of ultrasound. An ultrasonic lens can be used to direct ultrasonic rays from the transducer and an ultrasonic wave inhibitor structure can be used to prevent transmission of ultrasonic waves in an undesired direction.

In other systems, flow velocity measurement may be provided using non-Doppler means. In such cases, at least two electrodes can be mounted on a lead, with two of the electrodes each being formed of different biocompatible materials. One of these electrodes is formed as a polarizable electrode and is disposed in a detecting position (e.g., at or near the tricuspid valve) and another of these electrodes is located on the lead at an axially spaced distance from the polarizable electrode. In use, detection of over-voltage (caused by variation of ion distribution at the electrode-electrolyte interface) allows for a blood flow velocity signal to be generated.

As described above, blood flow within the heart has been conventionally monitored via a flow measurement sensor on the lead. Signals transmitted from the sensor to a cardiac medical device are in turn used to generate a flow waveform, e.g., via use of a controller within the device. The generated waveforms are often used to show velocity of the blood flowing through a region of the heart, e.g., through the tricuspid valve. In such cases, the controller within the device is responsive to the measured flow velocity, wherefrom the controller can detect heart irregularities and correspondingly control electrical pacing signals to the heart. For example, the flow waveform can be used for synchronization and control of ventricular cardiac pacing. As such, the early rapid diastolic filling wave (E-wave) as well as the late atrial diastolic filling wave (A-wave) can be measured from the generated flow waveforms. Ventricular pacing can then be synchronized with the A-wave. With such cardiac electrotherapy systems, improved and more reliable monitoring of cardiac activity has been achieved, resulting in improved pacing results.

In some cases, the above-described cardiac electrotherapy systems can involve pacemakers which, in normal atrial rhythm, act in a synchronous mode (VDD) and maintain atrio-ventricular synchronism, while only requiring implantation of a single lead. Blood flow velocity measurements can be used in providing rate responsive ventricular pacing and reliable means for atrial fibrillation detection. In addition, continuous monitoring of the right ventricular filling dynamics can be provided in order to estimate the ventricular muscle performance and/or to automatically reprogram the maximum tracking rate in such a way as to prevent angina pectoris and high-rate induced myocardial ischemia. Thus, the above-described cardiac electrotherapy systems, via their flow measurement functionality, can be used to detect a wide variety of cardiac deficiencies, each of which may signify a differing arrhythmic event. For example, the systems can be configured to further identify single premature ventricular contractions, discriminate between sinus tachycardia and pathologic tachycardia, confirm ventricular capture, detect right ventricular failure, etc.

To date, the above systems have generally been limited to acute rather than chronic applications. One reason for this involves tissue which, over time, is found to surround the leads of an implantable medical device. As is known, such fibrous tissue naturally grows or accumulates on the implanted portion of the leads and their corresponding connector assemblies. In turn, body fluid (e.g., water) stemming from such tissue (as well as from blood surrounding the leads) is often found to penetrate the insulative jackets on the leads, resulting in a change in impedance across the lead and connectors. This impedance change can be found to have an adverse effect on the transmittance of the signals along the lead as well as on the signal processing circuitry within the cardiac device. However, the presence of such tissue and/or blood around the leads (and their resulting adverse effect on the leads) is not as prevalent in acute applications because the period of implantation is often short (e.g., ranging from weeks to months) compared to chronic applications in which the period of implantation is much longer (e.g., ranging in years). Therefore, to date, the above limitations have mainly been identified when using the above systems in chronic applications.

What are needed are apparatus and systematic methods to overcome the above limitations so as to enable the above-described cardiac electrotherapy systems to be applicably used in both acute and chronic applications.

DESCRIPTION OF THE DRAWINGS

The following drawings are illustrative of particular embodiments of the present invention and therefore do not limit the scope of the invention. The drawings are not to scale (unless so stated) and are intended for use in conjunction with the explanations in the following detailed description. Embodiments of the present invention will hereinafter be described in conjunction with the appended drawings, wherein like numerals denote like elements.

DETAILED DESCRIPTION

Figure 1:
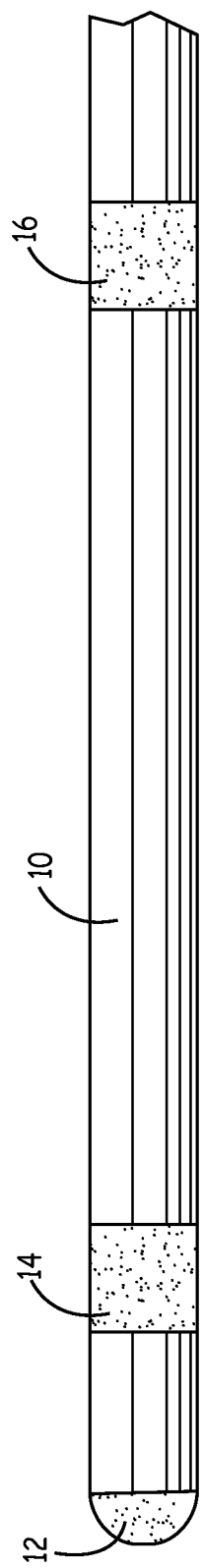
FIG. 1 is a perspective side view of a distal end of a lead having an exemplary flow measurement sensor arrangement provided thereon.

The following detailed description should be read with reference to the drawings, in which like elements in different drawings are numbered identically. The drawings depict selected embodiments and are not intended to limit the scope of the invention. It will be understood that embodiments shown in the drawings and described below are merely for illustrative purposes, and are not intended to limit the scope of the invention as defined in the claims. In addition, it should be appreciated that the techniques and methods described and illustrated herein can be implemented within a medical device in a variety of manners. For example, in certain embodiments, instructions corresponding to one or more of the techniques and methods are programmed within a controller (e.g., a processor) within such medical device. One skilled in the art would be familiar with such programming practices as well as other typical manners of implementation within medical devices. In turn, such manners of implementation are not discussed in further detail herein.

While systems and techniques may be collectively described herein, it should be appreciated that they can be used individually or in any combination with respect to their implementation in medical devices. In addition, while the systems and techniques are embodied herein with respect to cardiac medical devices, the invention should not be limited to such. To the contrary, any medical device designed to use flow measurement as a variable in providing a therapeutic response would fall within the spirit of the invention. Also, while the apparatus and techniques are embodied herein with respect to measuring the flow velocity of blood, the invention is equally applicable not only for measuring different characteristics of the blood flow, but also for measuring the flow of other fluids passing through regions of the body. Further, while the embodiments herein depict use of a polarizable electrode for the flow measurement device (i.e., via non-Doppler means), it should be appreciated that the embodiments could just as well use Doppler means, as exemplified above. Additionally, while body fluid (e.g., water) is described herein as stemming from tissue surrounding the implanted lead portions, it should be appreciated that such body fluid may also stem from a variety of other sources within the body proximate to the implanted portions of the leads, e.g., blood flowing around the leads.

FIG. 1 illustrates a distal end of a lead 10 having an exemplary flow measurement sensor arrangement positioned thereon. The lead 10 includes three electrodes 12, 14, and 16, wherein one of the electrodes, e.g., the electrode 16, can be formed of noble metal, thereby forming a polarizable electrode. The electrodes 12 and 14 can be respectively used for cardiac pacing and for sensing of the ventricular potential. In the steady state of an ionic media or fluid (e.g., such as blood), positive DC voltage can be measured on the electrode 16 using the electrode 14 (i.e., the indifferent electrode) as a reference. However, any other electrode within the electrolyte, e.g., the pacing electrode 12, may alternatively be used as a reference electrode. As briefly described above, as the ionic media flows around the lead 10, concentration over-voltage consequently occurs on the electrode 16, wherein the voltage measured includes a DC component (representing the galvanic potential) and an AC component (representing the consequence of flow variation). Fluctuation in the over-voltage is known to be a function of variation in flow velocity magnitude of the ionic media. As such, variance in the over-voltage occurring on the electrode 16 over time can be used to derive flow velocity rate of change of the ionic media.

Figure 2:
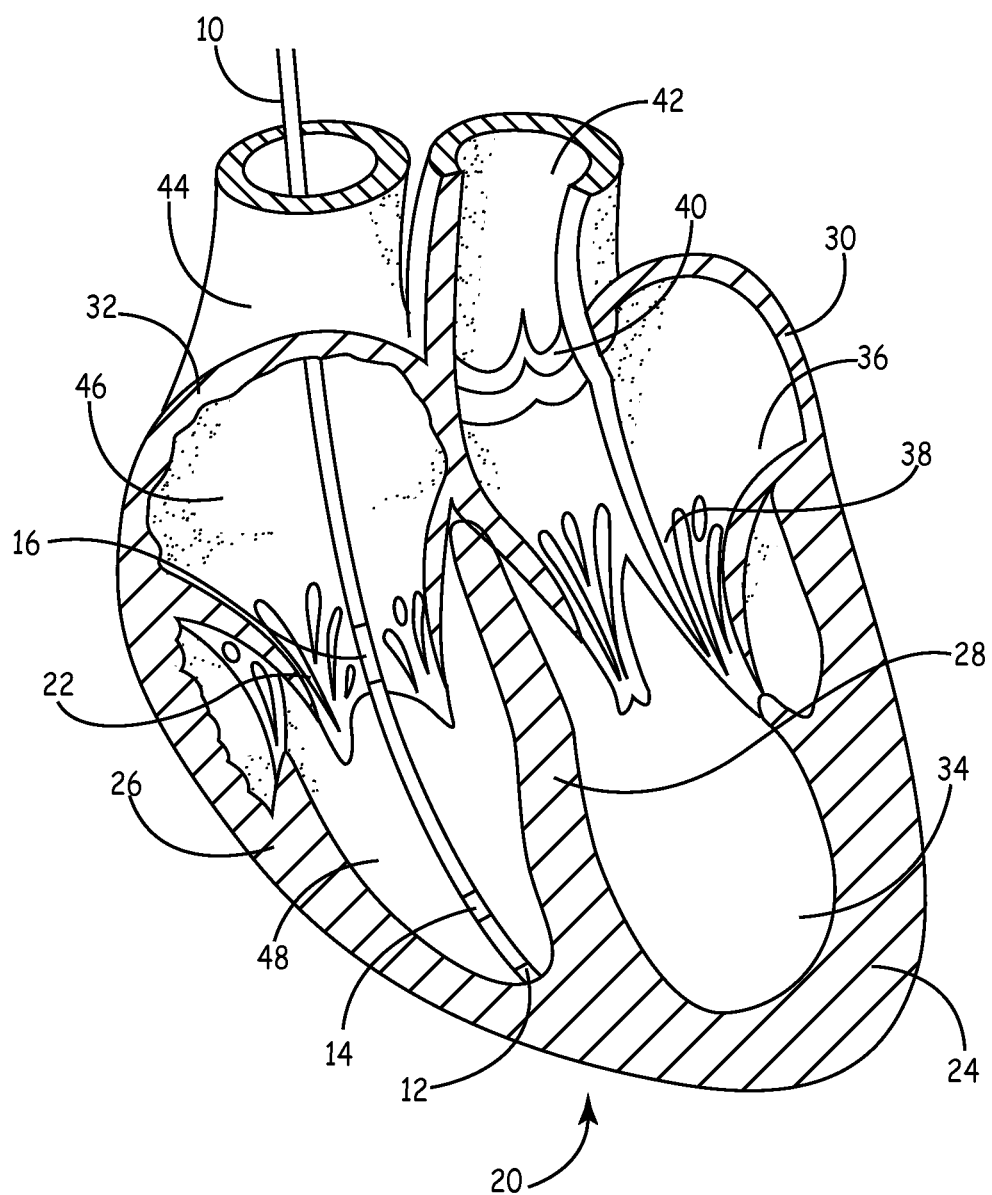
FIG. 2 is a cross-sectional side view of a human heart showing the lead of FIG. 1 exemplarily implanted therein.

FIG. 2 shows positioning of the lead 10 of FIG. 1 within a heart 20. As shown, in certain embodiments, the polarizable electrode 16 is positioned in the proximity of the tricuspid valve 22. The heart 20 is illustrated in a four chamber cross-sectional view, with the myocardial cross-section of each of the left-ventricular wall 24, the right ventricular wall 26, the interventricular septum 28, the left-atrial wall 30 and the right-atrial wall 32 being visible. The two chambers of the left side of the heart, i.e., the left ventricle 34 and left atrium 36, are separated by the mitral valve 38. The left ventricular outflow tract includes the aortic valve 40 and aorta 42. As shown, the lead body 10 can be implanted using the right side of the heart. In certain embodiments, the lead body 10 is passed through the vena cava superior 44 and the right atrium 46 into the right ventricle 48, with its active pacing electrode 12 located in the apex of the right ventricle 48. In certain embodiments, the polarizable electrode 16 is positioned in the lower right-atrial region, e.g., in the proximity of the tricuspid valve 22. The indifferent electrode 14 and pacing electrode 12 are further mounted adjacently to each other forming a bipolar pacing electrode system.

The blood inflow from the right atrium 46 into the right ventricle 48, i.e., through the tricuspid valve 22, causes a variation of the concentration of ions in vicinity of the polarizable electrode 16. Accordingly, over-voltage, measured between the electrode 16 and a certain reference electrode within the human body, e.g., the indifferent electrode 14, occurs. Although the reference electrode in this embodiment is exemplified as the electrode 14 (which is located within the heart 20), the reference electrode could alternatively be located in another part of the human body outside of the detecting area. As described above, the variation of said over-voltage can be used in determining the variation of blood flow. In this example, a bipolar pacing system is disclosed and therefore the indifferent electrode 14 can be used as a reference electrode for the over-voltage measurement. Alternatively, in certain embodiments involving a unipolar pacing system, the electrode 14 would not be required, and the over-voltage can instead be measured between the polarizable electrode 16 and the medical device case (not shown).

As described above, the over-voltage measured from a flow measurement sensor correspondingly varies with the flow velocity of the blood proximate the flow measurement sensor. Over-voltage signals transmitted to the cardiac device from the flow measurement sensor are in turn processed and provided as flow waveforms through use of a controller, e.g., a processor. The flow waveforms can then be analyzed by the device, via use of the controller, in detecting heart irregularities and/or cardiac arrhythmic events. As should be appreciated, the signals transmitted back to the cardiac device must be pre-conditioned prior to their being provided as flow waveforms. Such signal processing generally involves the use of electrical circuits, as described below.

Figure 3:
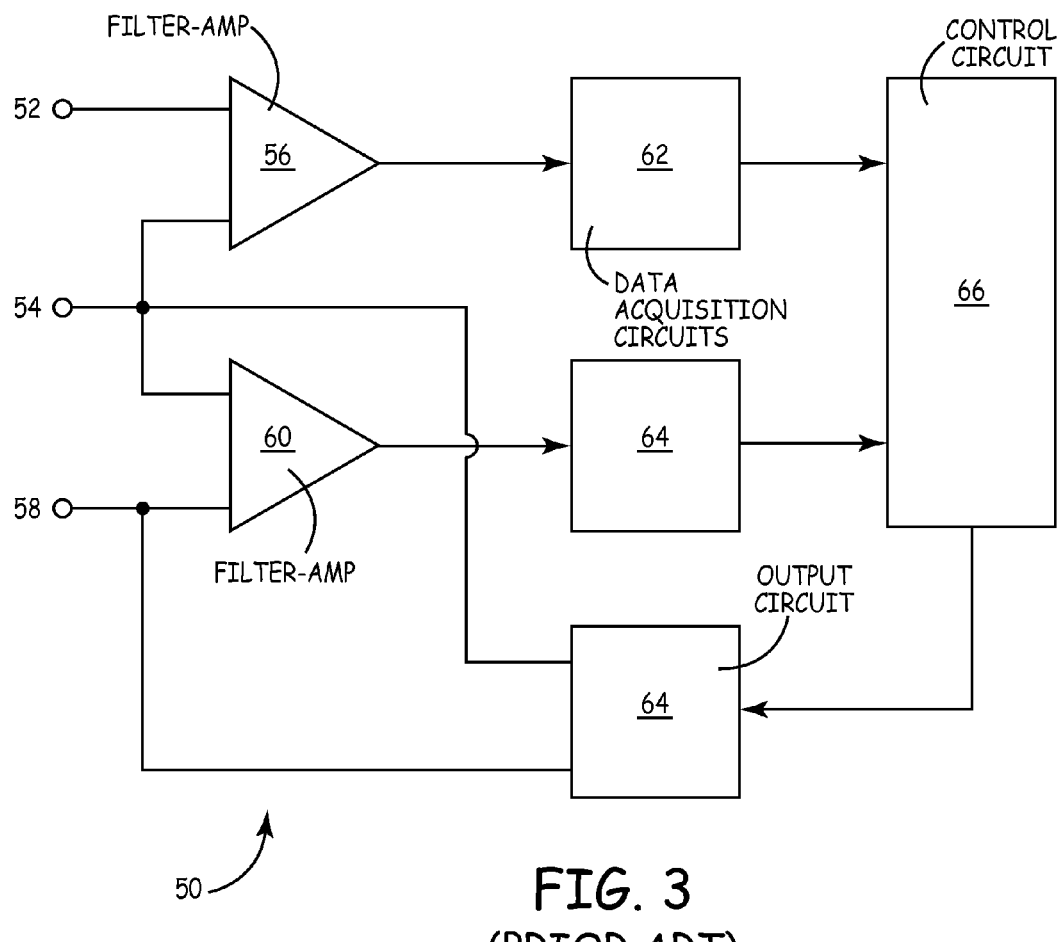
FIG. 3 is a block diagram of an exemplary VDD pacemaker circuit used with the lead of FIG. 1.

FIG. 3 illustrates an exemplary electrical circuit 50 of a single lead VDD pacemaker as used in conventional cardiac electrotherapy systems having flow velocity measurement capability. With reference to FIGS. 1 and 2, the signal occurring on the over-voltage sensing electrode 16 (e.g., detected with reference to electrode 14) is transmitted via respective electrical conductors of the lead 10 to the proximal terminals 52 and 54, forming the inputs to AC filter-amplifier 56. The filter-amplifier 56 has a bandpass frequency characteristic in order to amplify only the frequency spectrum of the AC voltage produced by the blood flow velocity variation, as well as to prevent the saturation by the galvanic DC potential. The signal of the bipolar pacing-sensing electrode 12/14 of the lead 10 is transmitted via terminals 58 and 54 to the input of filter-amplifier 60. The filter-amplifier 60 has a bandpass frequency characteristic in order to amplify only the frequency spectrum of the intracardiac ECG, as is generally known in the art.

Outputs of the filter-amplifiers 56 and 60 are led to the input of data acquisition circuits 62 and 64 respectively, wherein signal processing occurs, and further to a logic and control circuit 66. The filter-amplifier 56 processes the signal of the concentration over-voltage superimposed with ventricular intracardiac electrogram, while the filter-amplifier 60 processes only the intracardiac electrogram signal. Output circuit 68, which is connected to terminals 58 and 54, is often a pacing pulse generator. The logic and control circuit 66 generates the blanking period of both filter-amplifiers 56, 60 during the pacing pulse release by the pulse generator 68, as it is generally known, in order to prevent the sensing of the pacing pulse voltage and consequent polarization voltage by the filter-amplifiers 56, 60. Moreover, it generates a special sensing blanking period of only the filter-amplifier 56 during the sensing of an intracardiac electrogram by the filter-amplifier 60 in such a way as to avoid the misinterpretation of an electrogram signal detected by the bipolar electrode 16/14 as a signal of the blood flow. The same type of blanking period would be also useful in unipolar pacing system wherein the sensing of intracardiac EGM occurs both between the electrode 16 and pacemaker case as well as between pacing electrode 12 and pacemaker case.

The utility of the tricuspid flow measurement for the purpose of cardiac pacing regulation and control has been described in U.S. Pat. Nos. 5,243,976 and 5,316,001, the disclosures of which are incorporated by reference herein in relevant part. Further electrotherapy control systems featuring alternative flow velocity measurement sensor arrangements and their use have been described in U.S. Pat. No. 5,799,350, the disclosure of which is incorporated herein in relevant part. One of these sensor arrangements along with its corresponding signal processing circuitry are exemplarily provided herein with respect to FIGS. 1-3. However, it should be appreciated that the invention is not limited to such, but instead is applicable to any flow measurement design described and illustrated in the above-referenced patents as well as other designs known to those skilled in the art.

As described above, the above systems have been limited in terms of their accuracy when measuring flow for long term electrotherapy control. As exemplified above with respect to FIGS. 1-3, electrotherapy control systems with flow velocity measurement capability have been conventionally designed to include electrodes mounted on a lead, e.g., a pacing lead. In turn, signals, e.g., over-voltage signals, from the flow measurement electrodes are transmitted back to circuitry within the cardiac medical device case, whereat the signals are pre-conditioned and from such, flow waveforms are generated. Subsequently, the flow waveforms are analyzed for control of electrotherapy, e.g., via a controller.

However, as further described above, tissue is found to accumulate over time on the implanted portions of the lead of the cardiac medical device. As a result, body fluid (e.g., water) from the tissue can be found to penetrate the insulating jacket of the lead, leading to a decrease in impedance on the lead conductors. In acute applications (e.g., whereby implantation period can range from weeks to months), the amount of fibrous tissue that accumulates on the leads is often limited. Further, the period of exposure of the leads to the tissue and blood surrounding the leads is limited in such acute applications. Consequently, body fluid penetration with respect to the lead insulating jacket is typically not an issue. However, because chronic applications generally involve much longer periods of implantation (e.g., often five to seven years), such penetration is found to be more prominent, and has been found to adversely affect the flow measurement functionality of the system. In particular, as described above, penetration of body fluid into the insulating casing of the implanted lead has been found to have an adverse effect on the transmission of the signals along the lead as well as on the signal processing circuitry within the cardiac device, as further described below. Moreover, movements, e.g., bending, of the lead body causes variation of the impedance, whereby a lead bending signal is added as an artifact superimposed on the flow signal.

Figure 5:
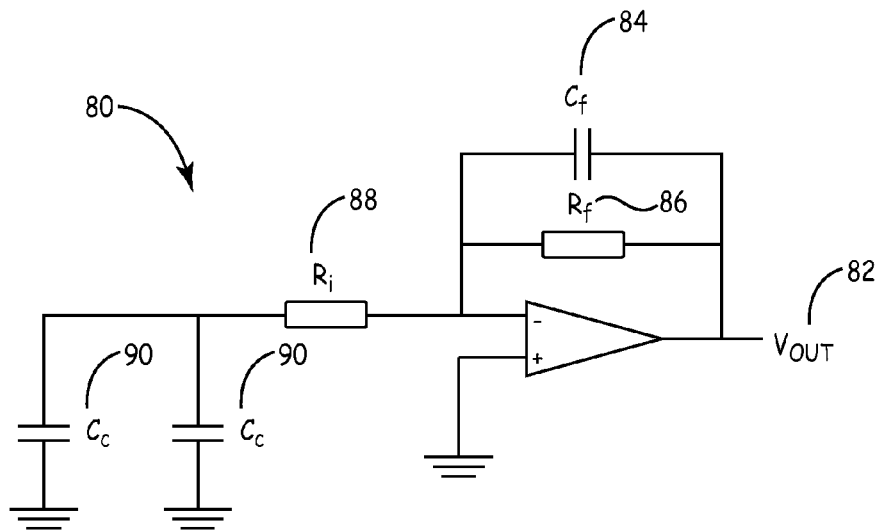
FIG. 5 is a basic configuration of a charge amplifier in accordance with certain embodiments of the invention.

As should be appreciated, the filter-amplifiers 56, 60 shown in the circuit 50 of FIG. 3 generally take the form of charge amplifier 80 shown in FIG. 5. As such, each of the filter-amplifiers 56, 60 has a feedback capacitor ($C_f$) 84 that is sized to dictate the output voltage of the amplifiers 56, 60, as further described below. Likewise, each of the filter-amplifiers uses the $C_f$ 84 and properly sized input capacitors ($C_e$) 90 and ($C_c$) 92 as well as properly sized input and feedback resistors ($R_i$) 88 and ($R_f$) 86, respectively, to dictate the low and high frequency cutoffs of the amplifiers 56, 60, as also further described below. However, as described above, in chronic applications, body fluid can be found to penetrate the insulation and/or the connector assemblies of the lead 10 operatively connected to the amplifiers 56, 60. As described above, such penetration decreases the impedance over the conductors of the lead 10, thereby resulting in a variation in the input capacitance to the amplifiers 56, 60. As should be appreciated, the variation in capacitance loads up the amplifiers 56, 60, thereby adversely affecting their use in processing the transmitted signals.

Figure 4:
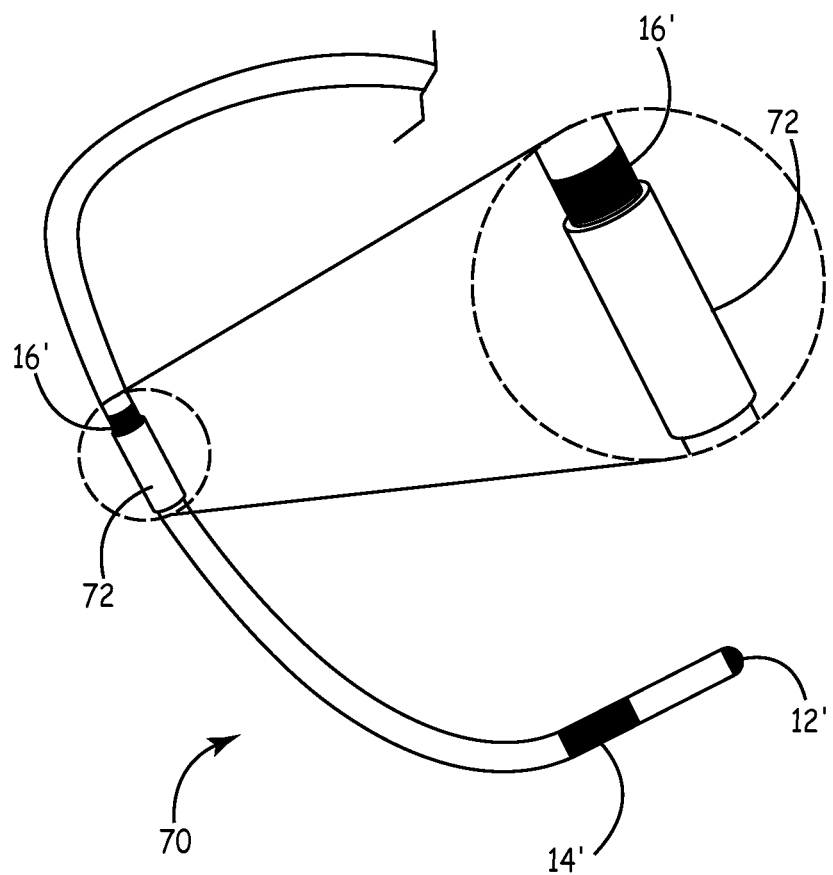
FIG. 4 is a perspective side view of a distal end of a lead having a flow measurement sensor arrangement in accordance with certain embodiments of the invention.

In addressing the above limitation of conventional systems, certain embodiments of the invention involve a lead having a capsule positioned thereon. FIG. 4 illustrates such a lead 70 with capsule 72 in accordance with certain embodiments of the invention. As shown, in certain embodiments, the lead 70 is similarly configured to the lead 10 already described herein with respect to FIG. 1, thereby including a pacing electrode 12', an indifferent electrode 14', and polarizable electrode 16'; however, as described herein, the invention should not be limited to such flow measurement sensor arrangement. Consequently, the functioning of the electrodes 12', 14', and 16' of the lead 70 is similar to that already described herein with respect to the lead 10 of FIG. 1. Likewise, the lead 70 can be implanted in a patient's heart as already described and illustrated herein in FIG. 2 (with respect to the lead 10 of FIG. 1) so as to measure blood flow velocity proximate to the polarizable electrode 16'.

However, in contrast to the lead 10 of FIGS. 1 and 2, the lead 70 of FIG. 4 includes the capsule 72. As shown in the enlarged view of the capsule 72 in FIG. 4, the capsule 72, in certain embodiments, surrounds a portion of the lead 70 as well as at least a portion of the flow measurement sensor, e.g., the polarizable electrode 16'. In certain embodiments, the capsule 72 forms an insulative shell on the lead 70 that is biocompatible with fibrous tissue forming thereon (and other tissue or blood surrounding the lead 70), yet resistant against penetration of water stemming from such tissue. Accordingly, in certain embodiments, the capsule 72 can be formed of such an insulative, biocompatible, water resistant material, such as high grade plastics or silicones; however, the invention should not be limited to such. For example, in certain embodiments, the capsule 72 may be coated with such a material.

In certain embodiments, the capsule 72 forms an assembly including both a portion of the flow measurement sensor, e.g., electrode 16', and the corresponding electrical circuitry used for signal processing (not visibly shown as the circuitry is positioned within the capsule 72). In certain embodiments, such corresponding electrical circuitry at least includes the filter-amplifier 56 of FIG. 3, and optionally, the corresponding data acquisition circuit 62; however, the electrical circuitry can also include the filter-amplifier circuit 60 of FIG. 3, and optionally, the corresponding data acquisition circuit 64 of FIG. 3 as well. Accordingly, as over-voltage occurs on the electrode 16', the electrode 16' transmits signals to the electrical circuitry housed within the capsule 72. As mentioned above, the flow measurement device can alternatively include other flow measurement sensor arrangements generally known. For example, in certain embodiments, the flow measurement sensor can involve a Doppler ultrasonic transducer (as briefly described above and detailed in more depth in U.S. Pat. Nos. 5,243,976 and 5,316,001), whereby both of the flow measurement electrodes are located in the tricuspid valve region of the heart.

Relocating the electrical circuitry from inside the cardiac device case (as illustrated in FIG. 3) onto the lead 70 helps address some of the above-described limitations found with conventional cardiac electrotherapy systems when used in chronic applications. For example, by shortening the distance between the polarizable electrode 16' and the electrical circuitry, the effect that the impedance on the lead conductors has on the signals transmitted between the electrode 16' and the corresponding electrical circuitry is limited. Furthermore, by locating the electrical circuitry within the capsule 72, the influence of the lead conductor impedance on signal transmittance between the sensor electrode 16' and the electrical circuits can be minimized. For example, by housing the electrical circuitry within the capsule 72 and forming an assembly between the electrode 16' and the capsule 72, the signals transmitted from the electrode 16' to the electrical circuitry do not need to pass along the conductors of the lead 70. Thus, any impedance variation on the lead conductors is prevented from directly (and adversely) affecting the source capacitance of the filter-amplifier 56.

In addition, by including digitizing circuitry (e.g., such as the data acquisition circuit 62 of FIG. 3) within the capsule 72, any adverse effect that the impedance variation on the lead conductors may have had on signals transmitted over the length of the lead 70 (from the circuitry within the capsule 72 to the medical device) can be minimized. For example, in certain embodiments, by positioning the data acquisition circuit 62 (along with the charge amplifier 56) within the capsule 72, the signals transmitted can be digitized prior to their being transmitted back to a controller or control circuit (e.g., such as control circuit 66 in FIG. 3) in the medical device case. As should be appreciated, through their digitization, the transmitted signals would have limited susceptibility to impedance variation on the conductors of the lead 70. This same relationship follows for the signals transmitted from and to the pacing electrode 12'. For example, as described above, in certain embodiments, the signal processing circuitry for the pacing electrode 12' (exemplarily shown in FIG. 3 as the filter-amplifier circuit 60 and the data acquisition circuit 64) can be positioned within the capsule 72. In turn, while there is still some separation between the electrode 12' and its corresponding electrical circuitry along the lead 70, the separation is much less than if the circuitry were housed in the medical device case (which is the conventional practice). In turn, signals transmitted from the electrical circuitry (housed in the capsule 72) corresponding to the pacing electrode 12' back to the medical device can be digitized (e.g., using the data acquisition circuit 64) so as to be less susceptible to impedance variation across the length of the lead between the capsule 72 and the medical device.

In summary, flow measurement systems in conventional cardiac electrotherapy systems have been found to be adversely affected by fibrous tissue accumulating on implanted portion of lead body. Particularly, in chronic applications, body fluid can be found to penetrate the insulation of the implanted leads, thereby decreasing the impedance of lead conductors. In turn, this impedance change is generally found to have an adverse effect with respect to its influence on corresponding electrical circuitry (used for signal processing) conventionally housed in the medical device as well as the signals being transmitted across the conductors of the leads. Certain embodiments of the invention have been described above to address such limitations. However, the accumulation of fibrous tissue and its impact on the electrodes of the flow measurement sensor can also be a concern, as described below.

As described above, overgrowth of tissue on the lead 70 and corresponding body fluid penetration therein can be found to adversely impact the flow measurement sensor on the lead 70. For example, with reference to FIG. 4, such tissue can be found to change the capacitance of the polarizable electrode 16' seen by its corresponding electrical circuitry (e.g., the filter-amplifier 56). In addition, impedance variation on the conductors of the lead 70 from penetration of body fluid into the insulation of the lead 70 can also be found to contribute to the capacitance of the electrode 16' changing. In turn, the functioning of the amplifier 56 (housed in the capsule 72) can be adversely affected.

Finally, tissue overgrowth on the lead 70, and particularly, on or proximate to the electrode 16', can adversely impact the measurement function of the electrode 16'.

39 In summary, the tissue overgrowth on the lead 70 and electrode 16' and the resulting variation in lead conductor impedance can often result in one or more of the above-described limitations concerning the electrode 16'. Consequently, the measurement of over-voltages by the electrode 16' as well as the processing of the signals transmitted by the electrode 16' to the amplifier 56 can be adversely affected. Thus, the validity of these measurements and processed signals can be compromised, e.g., in the corresponding cardiac electrotherapy systems. In certain embodiments, the electrical circuitry housed within the capsule 72 is configured to address this limitation, as further described below.

As briefly described above, FIG. 5 shows a basic configuration of the charge amplifier 80 in accordance with certain embodiments of the invention. The configuration of the amplifier 80 is built on the basis of an operational amplifier. Output voltage ($V_{out}$) 82 of the amplifier 80 is generally based on a ratio of input charge (q) to feedback capacitance (via $C_f$ 84), as shown by equation 1 below.

$$V_{out} = q/C_f \quad (1)$$

As is known, DC gain of the amplifier is zero, and product of the resistance of $R_f$ 86 and the capacitance of $C_f$ 84 sets the overall system time constant. Such relationship is shown by equation 2 below, whereby the time constant defines the low frequency cutoff ($f_l$) of the system.

$$f_l = 1/(2 \times \pi \times R_f \times C_f) \quad (2)$$

Accordingly, the values of $R_f$ 86 and $C_f$ 84 can be adjusted to produce required time constants and output sensitivities with respect to the amplifier 80.

When selecting operational amplifiers for charge pre-amplifier applications, as in the instant case, it is important to note that the resistance of $R_f$ 86 is generally very large (e.g., usually in the giga-ohm range). Because of this large resistance, leakage currents in the circuit can cause large voltage drops across $R_f$ 86, which can cause saturation of the amplifier 80. For this reason, as should be appreciated, low current leakage amplifiers are generally used and flux residue and other circuit board contaminants are minimized to prevent leakage current paths. In addition, circuit board material can also compromise circuit performance. Thus, the resistance of the circuit board must be significantly higher than $R_f$ 86 to maintain the low frequency cutoff set by $C_f$ 84 and $R_f$ 86. In some cases, ceramic based substrates can be used for their extremely high resistance characteristics; however, the invention should not be limited to such. For example, in other cases, as shown, a further resister $R_i$ 88 can be added in series with the input of the amplifier 80 to limit the high frequency response to a desirable range. In turn, as shown in equation 3 below, the high frequency −3 dB point of the amplifier 80 is:

$$f_h = 1/(2 \times \pi \times R_i \times (C_e + C_c)). \quad (3)$$

For general purpose amplifiers, as in this case, the value of $R_i$ 88 is kept small so that the frequency response is primarily dependent on the source capacity (via $C_e$ 90 and $C_c$ 92) of the sensor (e.g., the electrode 16'). In addition, as shown in equation 4 below, the voltage noise gain ($N_{out}$) of the amplifier 80 is the input voltage noise ($N_{in}$) amplified by the noise gain of the circuit.

$$N_{out} = N_{in} \cdot 3(1 + ((C_e + C_c)/C_f)) \quad (3)$$

As should be appreciated, with reference to both FIGS. 4 and 5, the source capacitance ($C_e$ 90 and $C_c$ 92) is generally a superimposition of capacitance of the electrodes implanted within the flow stream (i.e., 12', 14', and 16') and of capacitance of the lead 70. Accordingly, as alluded to above, if the lead 70 is standard or typical (not having reinforced insulation), penetration of water within silicone insulation of the lead 70 as well as fibrous tissue overgrowth on the flow measurement electrodes (16'/14') can be found to change the source capacitance ($C_e$ 90 and $C_c$ 92), and consequently, the high frequency cut-off frequency of the amplifier 80. Furthermore, the tissue overgrowth is generally found to decrease the flow signal (both from the flow measurement electrodes 16/14 on lead 10 of the conventional system exemplified in FIGS. 1-3 and from the capsule 72 of FIG. 4).

In addressing the above limitation of conventional systems, certain embodiments of the invention expand upon the capsule 72 configuration already described herein. Accordingly, in certain embodiments, the electrical circuitry housed within the capsule 72 includes a "tunable" charge amplifier which can be dynamically configured based on shift of source capacitance over chronic periods, as described above. In certain embodiments, such dynamic configuring can involve varying the values of $C_f$ 84, $R_f$ 86, and $R_i$ 88 of the amplifier 80 as warranted for proper and accurate processing of the signals transmitted thereto from the electrode 16'.

Figure 6:
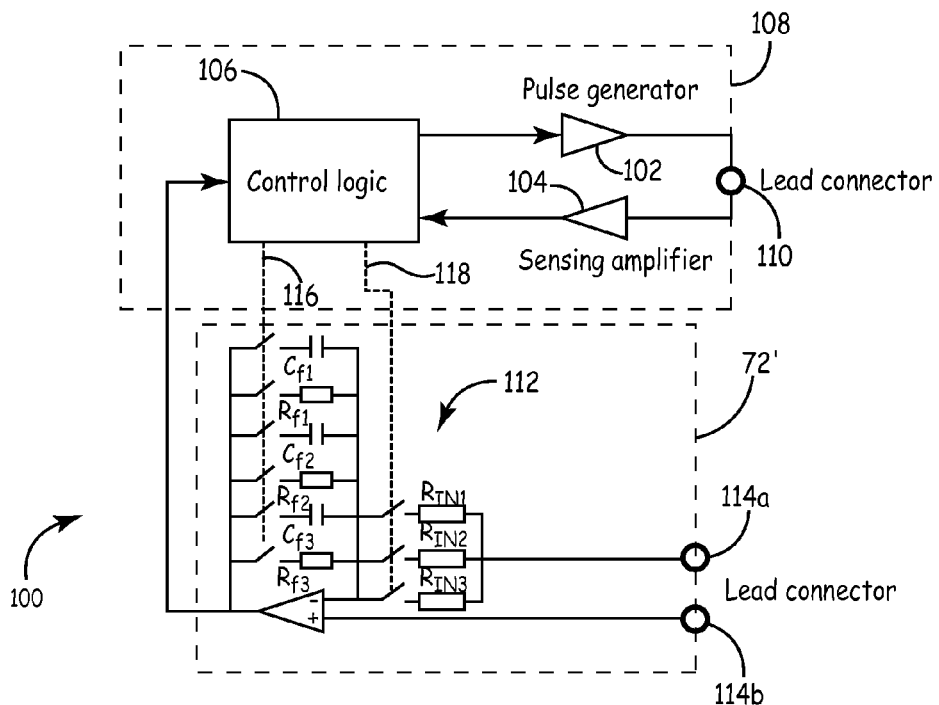
FIG. 6 is a block diagram of a circuit used in an implantable medical device having flow measurement capability in accordance with certain embodiments of the invention.

FIG. 6 illustrates a block diagram of a circuit 100 used in an implantable medical device having flow measurement capability in accordance with certain embodiments of the invention. The circuit 100 includes a pulse generator 102, a sensing amplifier 104, and control logic 106, which are generally housed within the medical device case 108. With reference to FIG. 4, the pulse generator 102 and sensing amplifier 104 are operatively connected to the pacing electrode 12' (via lead connector 110 and lead 70, which is not shown). In addition, in certain embodiments, the circuit 100 includes a charge amplifier 112 positioned on the lead 70 (not shown) and operatively connected between the flow measurement electrodes (via lead connectors 114a and 114b) and the control logic 106. As shown, in certain embodiments, the charge amplifier 112 is housed within a sensor flow capsule 72' (as detailed above). In certain embodiments, with reference to FIG. 4, the flow measurement electrodes would include polarizable electrode 16' and indifferent electrode 14'; however, the invention should not be limited to such configuration.

As described above, the flow measurement device can alternatively include other flow sensor configurations generally known. For example, in certain embodiments, the flow measurement configuration can involve a Doppler ultrasonic transducer (as briefly described above and detailed in more depth in U.S. Pat. Nos. 5,243,976 and 5,316,001), whereby both of the flow measurement electrodes would be located proximate to or within the tricuspid valve region of the heart. Using such an alternate flow sensor configuration can enhance functioning of the amplifier 112. For example, with the blood flow, there is a charge modulation at the metal-blood interface of the electrodes' surface. The amplifier 112 is often found to yield the signal produced by the charge modulation usually in the range of 1 picoCoulomb and 20 picoCoulomb. A balanced impedance pair of electrodes located together at the tricuspid valve region, despite their combined surface area, is generally found to yield a better signal-to-noise ratio than a single electrode relative to a large surface indifferent electrode.

In certain embodiments, the control logic 106 can be operatively connected to the charge amplifier 112 (via dashed connection 116 and/or dashed connection 118). As such, the control logic can be used to "tune" the amplifier 112 (as warranted). For example, in certain embodiments, the control logic 106 can be used to switch one or more of a plurality of feedback capacitors (exemplarily shown as $C_{f1}$, $C_{f2}$, and $C_{f3}$) and/or a plurality of feedback resistors (exemplarily shown as $R_{f1}$, $R_{f2}$, and $R_{f3}$), thereby programming the gain and the lower cutoff frequency of the amplifier 112 simultaneously. Additionally, in certain embodiments, the control logic 106 can be used to switch one or more of a plurality of input resistors (exemplarily shown as $R_{in1}$, $R_{in2}$, and $R_{in3}$), thereby adjusting the high frequency cutoff according to the source capacitance. As described above, with reference to FIG. 4, the source capacitance is imposed on the amplifier 112 from the electrodes 12', 14', 16' and the conductors of the lead 70.

Figure 7:
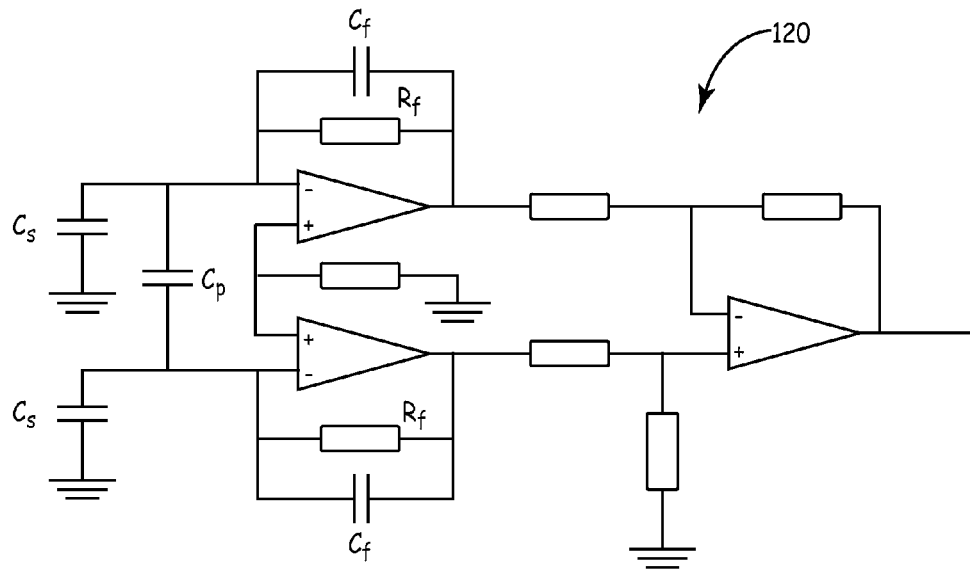
FIG. 7 is a block diagram of an exemplary differential charge amplifier in accordance with certain embodiments of the invention.

FIG. 7 shows a block diagram of an exemplary differential charge amplifier circuit 120. Such amplifiers are found to have significantly better common-mode rejection ratio (CMRR) than their basic charge amplifier counterparts, described herein with reference to amplifiers 56 and 60 of FIG. 3 and taking the form of the amplifier 80 of FIG. 5. Thus, in certain embodiments, the differential charge amplifier circuit 120 can be used in replacing at least the amplifier 56 of the electrical circuitry housed within the capsule 72 of FIG. 4. Such differential charge amplifiers are also found to yield excellent signal-to-noise ratio when the flow sensor comprises balanced impedance electrodes, as described above. Therefore, in certain embodiments, the differential charge amplifier circuit 120 replaces at least the amplifier 56 of the electrical circuitry housed within the capsule 72 of FIG. 4 and the non-Doppler flow measurement sensor is replaced by a Doppler ultrasonic transducer (as briefly described above and detailed in more depth in U.S. Pat. Nos. 5,243,976 and 5,316, 001).

Figure 8:
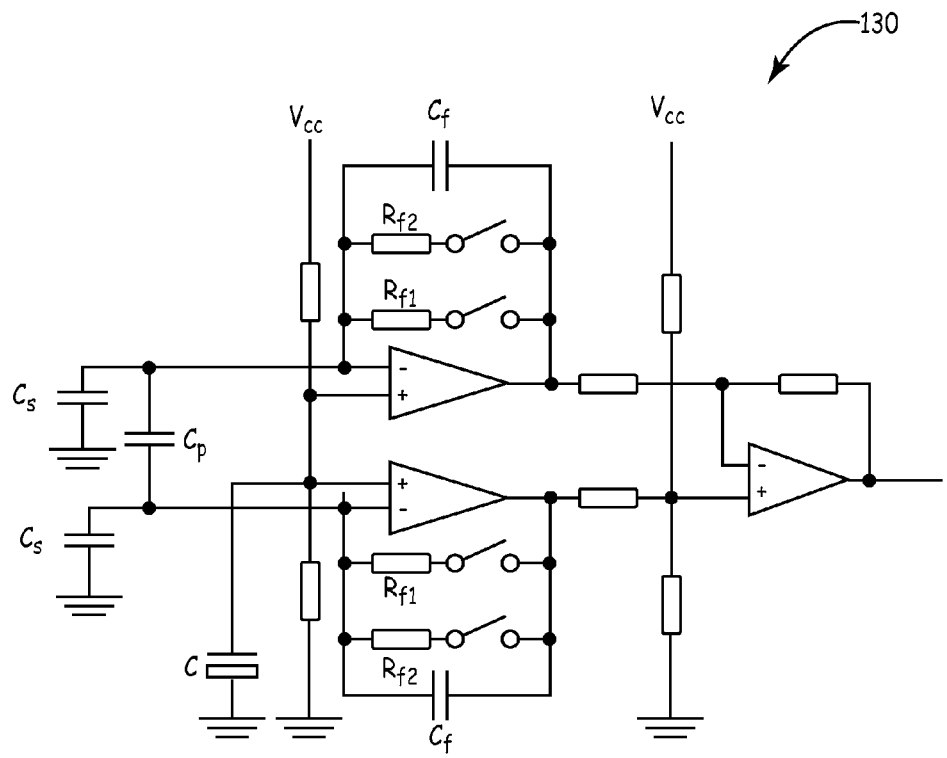
FIG. 8 is a block diagram of a further exemplary differential charge amplifier in accordance with certain embodiments of the invention.

FIG. 8 illustrates a block diagram of a further exemplary differential charge amplifier circuit 130. As shown, the design of the amplifier circuit 130 requires symmetric power supply ($V_{cc}$) to the amplifier circuit 130. In certain embodiments, the power supply can be provided via the implantable medical device's battery. In certain embodiments, as shown, the amplifier circuit 130 includes a plurality of feedback resistors (exemplarily shown as $R_{f1}$ and $R_{f2}$ on each side of the first layer of the amplifier circuit 130); however, the invention should not be limited to such. Instead, similar to what is represented in FIG. 6 with the amplifier 112, the feedback capacitors (shown as $C_f$ on each side of the first layer of the amplifier circuit 130) could also be represented as a plurality of capacitors. Further, a plurality of input resistors could be provided on each half of the same first layer of the amplifier circuit 130. In turn, the amplifier circuit 130 could be substituted for the amplifier circuit 112 of FIG. 6, whereby the feedback capacitance and resistance as well as the input resistance could be symmetrically varied across the first layer of the amplifier circuit 130 via the control logic 106. Accordingly, the gain and lower cutoff frequency as well as the high cutoff frequency of the amplifier circuit 130 could be varied to compensate for changes in source capacitance (e.g., via the electrodes 12', 14', 16' and the conductors of the lead 70, with reference to FIG. 4).

Figure 9:
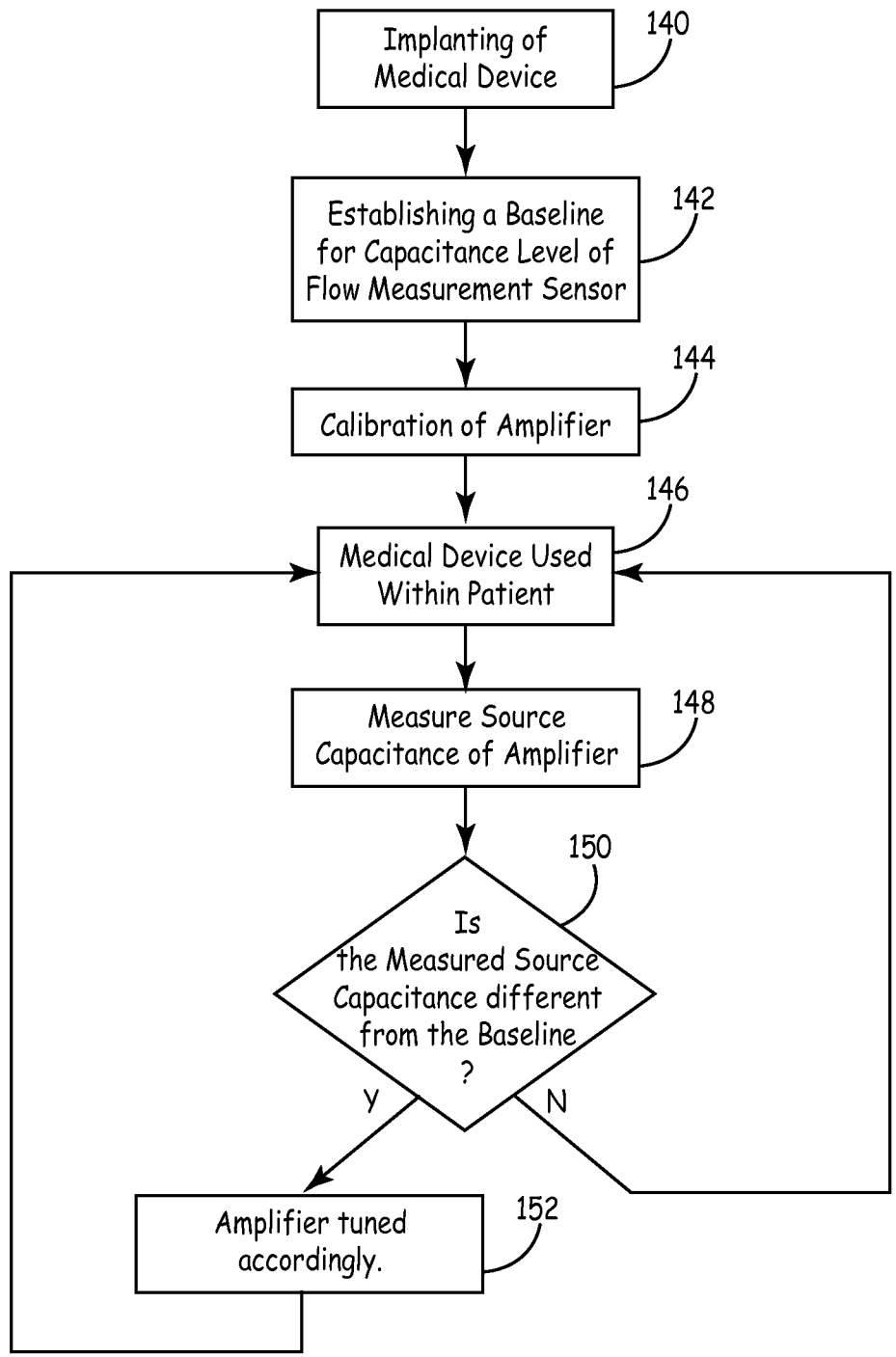
FIG. 9 is a flowchart depicting steps for initial calibration and subsequent tuning of a charge amplifier in the implantable medical device of FIG. 6 in accordance with certain embodiments of the invention.

FIG. 9 is a flowchart depicting steps for initial calibration and subsequent tuning of a charge amplifier in an implantable medical device having flow measurement capability in accordance with certain embodiments of the invention. For example, with reference to the circuit 100 of FIG. 6, the flowchart provides steps for tuning the amplifier 112 at different stages of use of the medical device. It should be appreciated that the steps would also be applicable to the differential charge amplifier circuit 130 of FIG. 8 being substituted for the amplifier 112 in the circuit 100. As further detailed below, the amplifier 112 would be initially calibrated upon implant and subsequently tuned so as to configure the amplifier 112 for proper signal processing based on variations that have occurred over time (due to fibrous tissue overgrowth) with respect to the capacitance of the sensor.

Step 140 of the flowchart of FIG. 9 involves implantation of the medical device within the patient. As should be appreciated, this involves implantation of at least one lead (stemming from the medical device) carrying the flow measurement sensor. While such lead stemming from the medical device is implanted, the medical device itself may or may not be further implanted (e.g., the medical device may be designed to remain outside the patient, as in the case of an external medical device). As described herein, the flow measurement sensor can involve any of a wide variety of known flow measurement sensor arrangements, including Doppler and non-Doppler configurations, which employ electrodes for measuring ionic media flow. If the flow measurement sensor is part of a cardiac electrotherapy system, one or more of these electrodes (depending on the flow measurement sensor configuration) are generally positioned in the region of the tricuspid valve of the heart. Certain embodiments described herein, e.g., with respect to FIG. 4, involve a capsule 72 being situated on the implanted lead proximate to the electrodes placed in the tricuspid valve region, thereby forming an assembly with these electrodes and corresponding electrical circuitry housed within the capsule 72.

Following implantation of the lead carrying the flow measurement sensor, step 142 involves establishing a baseline for the capacitance level of the sensor at implant. In certain embodiments, this can involve driving the flow measurement sensor with an AC voltage and measuring the current that is fed back through the lead. As should be appreciated, from this response of the sensor, one can measure the impedance of the sensor, which can be related to the capacitance of the sensor as well as of the lead conductor (referenced as the source capacitance). Upon determining the initial or baseline source capacitance at implant, the amplifier 112 is calibrated in step 144. Accordingly, values are calculated for the feedback capacitance and resistance as well as the input resistance of the amplifier 112 in order for the amplifier 112 to exhibit the desired gain (maximizing the output voltage range) and high and low cutoff frequencies (defining a practical frequency spectrum). Such calculations are known to the skilled artisan; as such, no further detail is provided herein. In turn, the proper switches of the amplifier 112 would be opened and closed to achieve these calculated capacitance and resistance values.

Following step 144, the medical device in step 146 is used within the patient. As described herein, if the medical device involves a cardiac electrotherapy system, the flow of ionic media would be measured in the tricuspid region of the patient's heart, e.g., in order to identify any of a variety of heart deficiencies or arrhythmias. Provided that the medical device is for chronic use, the medical device is programmed to periodically tune the amplifier 112. For example, in certain embodiments, the amplifier 112 may be tuned yearly; however, the schedule for tuning the amplifier can be programmed as desired via the logic control 106. Accordingly, the medical device via the control logic 106 will measure the source capacitance after some period of use in step 148. As should be appreciated, this measurement process is similar to that already described above with respect to step 142.

Once the source capacitance is determined in step 148, it is compared in step 150 with the baseline value (as initially determined in step 142). As should be appreciated, any difference in source capacitance from the baseline value can be found to generally affect the accuracy of the flow measurement system. However, significant differences in the source capacitance from the baseline value can be found to greatly influence, and thereby adversely affect, the flow measurement system. As such, in certain embodiments, the control logic 106 may determine if calculated difference in source capacitance is significant enough to require tuning of the amplifier; however, the invention should not be limited to such. Instead, in certain embodiments, the amplifier can be tuned given any shift in source capacitance.

Accordingly, if the calculated source capacitance is not found to be different from the baseline value, step 150 loops back to step 146. However, if the calculated source capacitance is found to be different from the baseline value, the amplifier is tuned in step 152. As should be appreciated, to compensate for the capacitance change, one or more of the gain and cutoff frequencies for the amplifier 112 would be modified accordingly. For example, if the measured signal is found to have decreased by 50%, the gain of the amplifier 112 would need to be set to twice its original value. As such, the control logic 106 calculates, where applicable, new parameters for the feedback capacitance and resistance as well as the input resistance of the amplifier 112 in order for the amplifier 112 to compensate for the determined change in source capacitance. In turn, the proper switches of the amplifier 112 would be opened and closed to achieve these calculated capacitance and resistance values. Once the amplifier 112 is calibrated, step 152 loops back to step 146.

It will be appreciated the embodiments of the present invention can take many forms. The true essence and spirit of these embodiments of the invention are defined in the appended claims, and it is not intended the embodiment of the invention presented herein should limit the scope thereof.

What is claimed is:

1. A flow measurement system comprising:
   a medical device;
   a lead adapted for implantation within a patient;
   a flow measurement means, mounted on the lead, for detecting a flow parameter of ionic media at a detecting position in a selected detecting area when the lead is inserted into the patient;
   a capsule, positioned on the lead proximate to the flow measurement means, the flow measurement means comprising at least first and second electrodes, the capsule positioned on the lead proximate to at least the first electrode;
   electrical circuitry, housed within the capsule and operatively connected to the first electrode, for receiving and processing flow signals from the flow measurement means; and
   a plurality of electrical conductors contained in said lead, at least one conductor having a distal end operatively connected to the electrical circuitry and having a proximal end operatively connected to the medical device; and
      wherein the electrical circuitry comprises a charge amplifier, having one or more pluralities of feedback capacitors, feedback resistors, and input resistors, each of the pluralities connected to the charge amplifier via switches, the charge amplifier being configured to digitize the flow signals from the flow measurement means, said digitized flow signals being transmitted through the at least one conductor from the capsule to the medical device, and
      wherein the medical device comprises a control circuit operatively connected to the charge amplifier via one or more of the lead conductors, the control circuit adapted to periodically determine source capacitance of the charge amplifier and adapted to trigger one or more of the switches to adjust one or more of gain, low cutoff frequency, and high cutoff frequency of the amplifier to correspond with the determined source capacitance.

2. A system according to claim 1, wherein the medical device comprises a cardiac electrotherapy system, wherein the selected detecting area comprises the patient's heart, and wherein the ionic media comprises blood.

3. A system according to claim 2, wherein the detecting position comprises the tricuspid valve region of the patient's heart and the flow parameter comprises flow velocity.

4. A system according to claim 2, wherein the medical device houses a control circuit adapted to generate flow waveforms from processed signals transmitted from the electrical circuitry and adapted to interpret the flow waveforms in assessing irregularities with respect to functioning of the patient's heart.

5. A system according to claim 4, wherein the medical device comprises a pacemaker and the lead comprises a pacing lead having a third electrode mounted thereon and adapted for delivering electrical therapy to the patient's heart, wherein the pacemaker houses a pulse generator that is operatively connected to both the third electrode via another of the lead conductors and the control circuit, the control circuit programmed to control delivery of electrical therapy to the patient's heart via the pulse generator and the third electrode based on its interpretation of the generated flow waveforms.

6. A system according to claim 1, wherein the flow measurement means comprises a Doppler flow measurement configuration, the first and second electrodes being disposed in the detecting position and forming an annular piezo body for measuring the flow parameter by means of ultrasound.

7. A system according to claim 1, wherein the charge amplifier comprises a differential charge amplifier circuit.

8. A system according to claim 1, wherein the electrical circuitry comprises at least one data acquisition circuit operatively connected between the charge amplifier and the at least one conductor, the at least one data acquisition circuit adapted for digitizing processed flow signals from the charge amplifier and transmitting such digitized signals to the medical device via the at least one conductor.

9. A system according to claim 1, wherein the capsule has at least an outer surface formed of an insulative, biocompatible, water resistant material.

10. A flow measurement system comprising:
    a medical device;
    a lead adapted for implantation within a patient;
    a flow measurement means, mounted on an exterior surface of the lead, for detecting a flow parameter of ionic media at a detecting position in contact with the exterior surface of the lead when the lead is inserted into the patient;
    a capsule, positioned on the lead proximate to the flow measurement means, the flow measurement means comprising at least first and second electrodes, the capsule positioned on the lead proximate to at least the first electrode;
    electrical circuitry, housed within the capsule and operatively connected to the first electrode, for receiving and processing flow signals from the flow measurement means; and
    a plurality of electrical conductors contained in said lead, at least one conductor having a distal end operatively connected to the electrical circuitry and having a proximal end operatively connected to the medical device; and
       wherein the electrical circuitry comprises a charge amplifier that is configured to digitize the flow signals from the flow measurement means, said digitized flow signals being transmitted through the at least one conductor from the capsule to the medical device.

11. A flow measurement system comprising:
a medical device;
a lead adapted for implantation within a patient;
a flow measurement means, mounted on the lead, for detecting a flow parameter of ionic media at a detecting position in a selected detecting area when the lead is inserted into the patient;
a capsule, positioned on the lead proximate to the flow measurement means, the flow measurement means comprising at least first and second electrodes, the capsule positioned on the lead proximate to at least the first electrode;
electrical circuitry, housed within the capsule and operatively connected to the first electrode, for receiving and processing flow signals from the flow measurement means; and
a plurality of electrical conductors contained in said lead, at least one conductor having a distal end operatively connected to the electrical circuitry and having a proximal end operatively connected to the medical device; and
wherein the electrical circuitry comprises a charge amplifier that is configured to digitize the flow signals from the flow measurement means, said digitized flow signals being transmitted through the at least one conductor from the capsule to the medical device, and
wherein the medical device comprises a control circuit operatively connected to the charge amplifier via one or more of the lead conductors, the control circuit adapted to periodically determine source capacitance of the charge amplifier and adapted to adjust one or more of gain, low cutoff frequency, and high cutoff frequency of the amplifier to correspond with the determined source capacitance.

* * * * *